United States Patent [19]

Fucci et al.

[11] Patent Number: 5,366,468
[45] Date of Patent: Nov. 22, 1994

[54] DOUBLE BLADED SURGICAL ROUTER HAVING ASPIRATION PORTS WITHIN FLUTES

[75] Inventors: Joseph Fucci, Port Richey, Fla.; Terry L. Whipple, Richmond, Va.

[73] Assignee: Linvatec Corporation, Largo, Fla.

[21] Appl. No.: 149,447

[22] Filed: Nov. 9, 1993

[51] Int. Cl.$^5$ .............................................. A61B 17/32
[52] U.S. Cl. ................................... 606/180; 604/22; 606/170
[58] Field of Search ............... 606/159, 170, 180, 171; 604/22; 128/751–755; 30/29.5, 240, 263, 264, 265

[56] References Cited

U.S. PATENT DOCUMENTS

| | | |
|---|---|---|
| 703,063 | 6/1902 | Hawkins . |
| 2,707,329 | 5/1955 | Costoff . |
| 3,368,257 | 2/1968 | Andreasson . |
| 4,113,405 | 9/1978 | Dillinger . |
| 4,167,944 | 9/1979 | Banko ................................ 128/305 |
| 4,842,578 | 6/1989 | Johnson et al. . |
| 4,867,157 | 9/1989 | McGurk-Burlson et al. ....... 128/305 |
| 5,047,040 | 9/1991 | Simpson et al. ..................... 606/159 |
| 5,097,849 | 3/1992 | Kensey et al. ................... 606/180 X |
| 5,112,299 | 5/1992 | Pascaloff ............................. 604/22 |
| 5,147,376 | 9/1992 | Pianetti ............................... 606/170 |

FOREIGN PATENT DOCUMENTS

| | | |
|---|---|---|
| 1052375 | 9/1953 | France . |
| 3433570 | 3/1986 | Germany . |

OTHER PUBLICATIONS

V. Mueller Endoscopy PowerCut Snap-In Disposable Blades, Baxter Int'l Inc., Feb. 1992.

*Primary Examiner*—Stephen C. Pellegrino
*Assistant Examiner*—Nancy Mulcare

[57] ABSTRACT

A surgical router for cutting anatomical tissue includes an outer tubular member and an inner member rotatably disposed in said outer member and having a pair of router blades disposed distally of a distal end of the outer member and equally spaced about a longitudinal axis of the inner member and a pair of flutes disposed between the router blades. The flutes have bottoms and sides transverse to the flute bottoms, with the flute bottoms angularly intersecting a passage in the inner member to form aspiration ports within and integral with the flutes. The router blades have leading walls, trailing walls and clearance walls with a width between the trailing walls that is tapered in a distal direction. The leading walls correspond to the flute sides and are curved about the inner member axis in the direction of rotation of the inner member in the outer member. End and side cutting edges are disposed along the leading walls with the end cutting edges being curved about the inner member axis in accordance with the curvature of the leading walls, and the side cutting edges extending longitudinally, helically along the inner member. Center cutting surfaces join the clearance walls and the leading walls at notches at the inner member distal end, and the junctures of the center cutting surfaces with the clearance walls define center cutting edges angled from the end cutting edges in the direction of rotation of the inner member in the outer member.

33 Claims, 2 Drawing Sheets

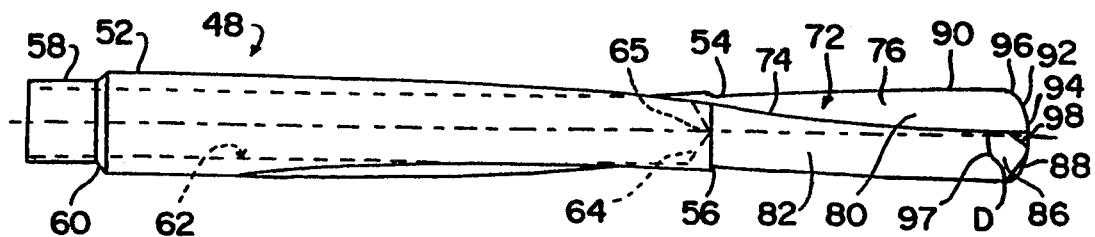
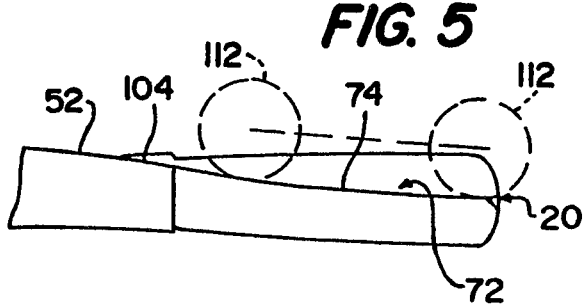
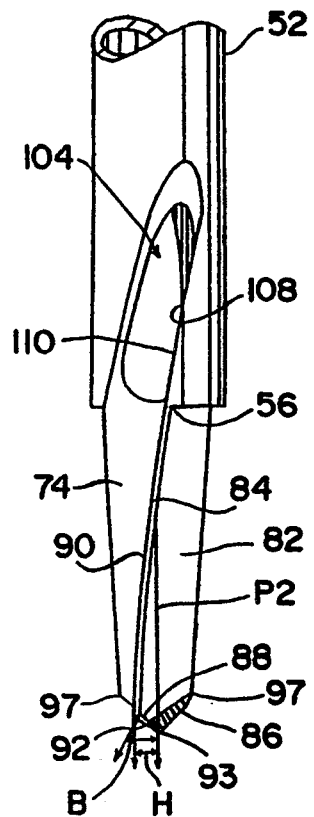
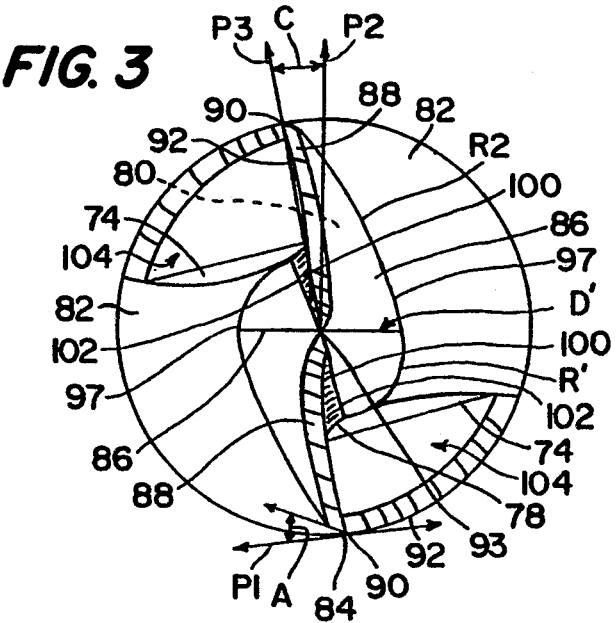

DOUBLE BLADED SURGICAL ROUTER HAVING ASPIRATION PORTS WITHIN FLUTES

BACKGROUND OF THE INVENTION

1. Field of the Invention

The present invention relates to surgical cutting instruments and, more particularly, to surgical routers having cutting blades for cutting anatomical tissue, aspiration ports for aspirating tissue cut by the cutting blades and flutes for carrying cut tissue toward the aspiration ports.

2. Description of the Prior Art

Surgical instruments for cutting various types of anatomical tissue have become extremely popular for use in many surgical procedures and, particularly, in joint surgery such as surgery of the knee and shoulder. Surgical cutting instruments for cutting anatomical tissue have been designed with cutting blades to perform various diverse cutting functions, such as resection, shaving and abrading, on various diverse types of anatomical tissue, such as bone and cartilage. Such surgical cutting instruments have also been designed with flutes to facilitate cutting by the cutting blades and with suction holes to aspirate tissue cut by the cutting blades via the surgical cutting instrument. One of the disadvantages of many presently available fluted surgical cutting instruments is that the structure and arrangement of the cutting blades and flutes with respect to one another fail to produce aggressive cutting and efficient resecting action in diverse types of anatomical tissue. Other disadvantages of fluted surgical cutting instruments are that the geometry of flutes and/or aspiration ports is not capable of accommodating relatively large quantities of tissue cut by the cutting blades and is not effective in carrying the cut tissue toward the suction holes, such that the instrument can become clogged during use. An additional drawback of many fluted surgical cutting instruments is that the suction holes are located away from the flutes with the result that the cut tissue can build up and clog the instrument prior to reaching the suction holes. Clogging of the surgical cutting instruments during use is highly undesirable in that impairment and/or interruption of surgical procedures, as well as damage to the cutting instruments, can result. In this regard, clogging of the surgical cutting instruments is particularly disadvantageous in endoscopic or closed surgery arthroscopic procedures. An additional disadvantage of such prior art instruments is that the surgical site becomes clouded from view with debris that is not resected but thrown radially outward due to the aspiration ports not being located sufficiently close to the blades. Accordingly, there is a need for a fluted surgical router, particularly in endoscopic procedures, for aggressively cutting and efficiently resecting various diverse types of anatomical tissue with various diverse cutting functions and for effectively carrying the cut tissue and debris toward aspiration ports of the surgical router for removal, via the surgical router, from the patient's body.

SUMMARY OF THE INVENTION

Accordingly, it is a primary object of the present invention to provide a surgical router overcoming the aforementioned disadvantages of prior art fluted surgical cutting instruments.

Another object of the present invention is to provide a surgical router including: an outer member; an inner member rotatably disposed in the outer member; a pair of cutting blades on the inner member disposed beyond a distal end of the outer member for cutting various diverse types of anatomical tissue; flutes disposed between the cutting blades for carrying tissue cut by the cutting blades; and aspiration ports within the flutes for aspirating the cut tissue through the surgical router.

A further object of the present invention is to provide an instrument of the type described with flutes having bottoms arranged transverse to the cutting blades and with aspiration ports disposed in the flute bottoms proximally of the cutting blades.

It is also an object of the present invention to provide a surgical router having connecting segments joining flute bottoms to flute sides, the connecting segments being curved about a longitudinal axis of the inner member in the direction of rotation of the inner member within the outer member.

The present invention has as another object to provide a surgical router having a passage in an inner member with flute bottoms angularly intersecting the passage to form aspiration ports.

An additional object of the present invention is to provide a surgical router having an inner member with leading walls defined by flute sides and end cutting edges and helical side cutting edges along the leading walls, the leading walls being curved about the inner member axis in the direction of rotation of the inner member in the outer member to permit cutting of anatomical tissue by the cutting edges.

Yet another object of the present invention is to provide a surgical router with trailing walls extending between flute bottoms and leading walls, and a distally tapered width between the trailing walls.

A still further object of the present invention is to provide a surgical router having clearance surfaces extending angularly, inwardly from the trailing walls at a pair of opposed ridges toward the inner member longitudinal axis.

The present invention has as an additional object to provide a pair of notches at a distal end of the surgical router between the clearance surfaces and the leading walls in communication with the flutes, the notches defining center cutting edges angled from the end cutting edges in the direction of rotation of the inner member in the outer member.

Some of the advantages of the present invention are: (a) tissue cut by the cutting blades and debris are immediately aspirated through the surgical router due to the aspiration ports being integral with the flutes; (b) various diverse types of anatomical tissue can be cut with the surgical router utilizing various diverse cutting functions without clogging by tissue and debris; (c) tissue cutting procedures are greatly enhanced; (d) the tapered profile and configuration of the router tip of the surgical router facilitates movement, manipulation and positioning of the router tip at a surgical or cutting site and relative to anatomical tissue to be cut; (e) the curved connecting segments deter build-up, load-up and clogging of the surgical router by tissue fragments and debris as well as clouding of the surgical site; (f) by forming the flutes to have an increasing width in the proximal direction, relatively large quantities of tissue fragments and debris can be captured and transported toward the aspiration ports; (g) the curved configuration of the leading walls about the inner member longitudinal axis increases the space available within the flutes to capture and transport tissue fragments and debris and facilitates cutting by the cutting edges; (h) the aspiration ports can be formed integrally, unitarily with the flutes, utilizing a relatively simple grinding process; (i) the aspiration ports can be elongate, oval or elliptical in shape in accordance with the angle at which the flute bottoms intersect the passage such that the aspiration ports can accommodate relatively large quantities of tissue fragments and debris as well as tissue fragments and debris that are relatively large in size; (j) end and center cutting can be easily initiated and accomplished with the surgical router; (k) the time required to perform tissue cutting procedures can De reduced; and (l) the surgical router according to the present invention is particularly useful in closed, or endoscopic, surgical procedures.

These and other objects, advantages and benefits are realized with the present invention as characterized in a surgical router including an outer tubular member having a distal end and a proximal end. An inner member is rotatably disposed in the outer member and has a pair of router blades thereon equally spaced about a longitudinal axis of the inner member and disposed beyond the distal end of the outer member for cutting anatomical tissue. A pair of flutes is disposed between the router blades for capturing anatomical tissue cut by the router blades. Aspiration ports within the flutes aspirate cut tissue and debris through the surgical router. Each of the flutes has a bottom and a side transverse to the bottom, and the flute bottoms angularly intersect a passage in the inner member to form the aspiration ports within and integral with the flutes. The flutes have a width corresponding to the width of the flute bottoms in a direction transverse to the flute sides, and the flute width increases from distal ends of the flutes toward proximal ends of the flutes. Curved connecting segments join the flute bottoms and sides and are curved about a longitudinal axis of the inner member in the direction of rotation of the inner member in the outer member. Each of the router blades has a leading wall defined by the side of an adjacent flute, and side and end cutting edges defined by the juncture of side and end cutting surfaces, respectively, with the leading wall. The leading walls are curved about the inner member longitudinal axis in the direction of rotation of the inner member, and the end cutting edges are curved about the inner member axis in accordance with the curvature of the leading walls. The side cutting edges merge with the end cutting edges at a major diametric dimension for the router blades, and the side cutting edges are helical, extending longitudinally along the inner member. The router blades have trailing walls extending between the flute bottoms and the side cutting surfaces, and a width between the trailing walls that is tapered in a distal direction. Clearance walls are joined to the trailing walls at opposed ridges and extend angularly, inwardly in the direction of the inner member axis such that the width of the inner member from the ridges toward a distal end of the inner member is also tapered. Notches are formed in the inner member between the clearance walls and the leading walls in communication with the flutes to define center cutting surfaces. Center cutting edges are defined by the juncture of the center cutting surfaces with the clearance walls. The center cutting edges extend angularly outwardly in a proximal direction from the inner member distal end, and are angled from the end cutting edges in the direction of rotation of the inner member in the outer member.

The above and still further objects, features and advantages of the present invention will become apparent upon consideration of the following detailed description of a specific embodiment thereof, particularly when considered in conjunction with the accompanying drawings wherein like reference numerals in the various figures are utilized to designate like components.

BRIEF DESCRIPTION OF THE DRAWINGS

FIG. 2 is an enlarged side view of the router tip of the surgical router of FIG. 1.

FIG. 3 is an enlarged front view of the router tip of FIG. 2.

FIG. 4 is a broken top view of the router tip of FIG. 2.

FIG. 5 is a broken side view illustrating a process for forming the flutes and aspiration ports of the router tip of FIG. 2.

DESCRIPTION OF THE PREFERRED EMBODIMENT

Figure 1:
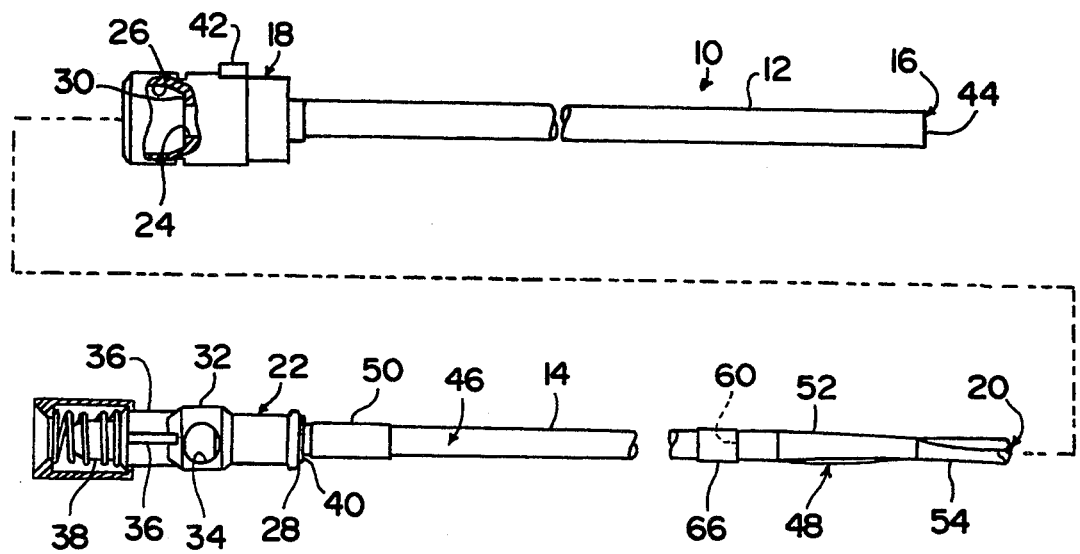
FIG. 1 is an exploded side view of the surgical router according to the present invention.

A surgical router according to the present invention is illustrated at 10 in FIG. 1 and includes an elongate outer tubular member 12 and an elongate inner member 14 rotatably disposed in outer tubular member 12. Outer member 12 has an open distal end 16 and an open proximal end secured to a hub 18. Inner member 14 is partly hollow or tubular or formed with an internal passage or channel as described further below, and has a distal end 20 and a proximal end secured to a hub 22. Hub 18 is preferably made of plastic and has a generally cylindrical configuration with a central bore 24 therethrough receiving the proximal end of outer member 12. A cylindrical recess 26 communicates with bore 24 for receiving hub 22 held in place therein by spring arms (not shown) in hub 18. Hub 22 is preferably made of plastic and is configured to be received in recess 26 with a forward lip 28 of hub 22 engaged with a bearing surface 30 in hub 18. Hub 22 includes an enlarged central barrel 32 having a transverse passage 34 extending therethrough in communication with an axial bore in hub 22 receiving the proximal end of inner member 14. Ribs 36 extend transverse to the axis of hub 22 and longitudinally in a proximal direction from barrel 32. A driven tang 38 extends longitudinally in the proximal direction from ribs 36 and is adapted to be coupled with a rotatable slotted drive shaft (not shown) of a motor of a handpiece (not shown). If desired, a thrust washer 40 can be disposed on inner member 14 adjacent a forward or distal facing surface of lip 28 for engaging bearing surface 30 when the inner member is assembled with the outer member. A locator stub 42 extends radially from hub 18 and is received in slots of the handpiece to secure hub 18 thereto. With the inner and outer members coupled to the handpiece, inner member 14 is rotatably driven within outer member 12 by the drive shaft while suction is produced in the lumen or passage of the inner member via suction channels in the handpiece communicating with a vacuum or suction source and transverse passage 34.

The structure of hubs 18 and 22 is described herein in general terms since the hubs correspond to those utilized in the Concept INTRA-ARC Drive System of Linvatec Incorporated, Concept Division, designed for rotating the inner member within the outer member as manually controlled by switches on the handpiece, the floor or a console supplying power to the handpiece. Reference is made hereto to the handpiece drive system of the Concept INTRA-ARC Drive System for more specific details relating to the structure and operation thereof. Although the surgical router of the present invention is shown and described for use in the Concept INTRA-ARC Drive System, it will be appreciated that the surgical router can have any desired hub configuration for use with any drive system or handpiece capable of rotating an elongate inner member within an elongate outer member while producing suction in the inner member.

Figure 7:
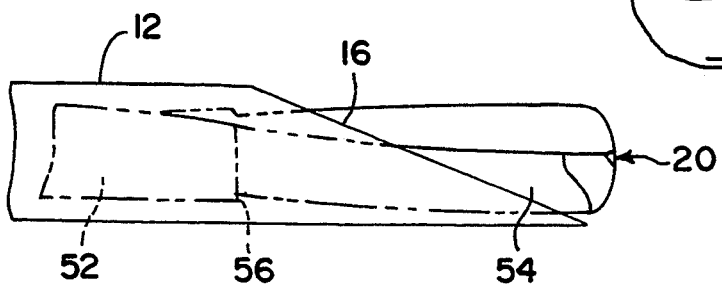
FIG. 7 is a broken side view of a modification of the surgical router illustrating the outer tubular member extending distally at an angle to the axial plane of the outer tubular member.

Outer tubular member 12 is preferably made of a length of stainless steel tubing with the proximal end thereof adhesively secured in bore 24 of hub 18 and the distal end 16 defining an annular peripheral edge 44 disposed in a plane perpendicular to a longitudinal axis of the outer member as shown in FIG. 1. Alternatively, the outer member distal end can be angled or "hooded" to define a somewhat oval or elliptical peripheral edge disposed in a plane at an acute angle with a longitudinal axis of the outer member as shown in FIG. 7, wherein the outer member extends distally at an angle to the axial plane of the outer member. Outer member 12 has a length such that a distal section of a router tip of inner member 14 protrudes distally beyond edge 44 when lip 28, or thrust washer 40, abuts bearing surface 30 as described below. Outer member 12 has an inner diameter to closely receive inner member 14 with minimal gap or clearance therebetween while allowing the inner member to rotate freely within the outer member when driven by the drive shaft. If desired, the proximal end of outer member 12 can be externally knurled to enhance securement of the outer member to hub 18.

Inner member 14 is made up of a body 46 and a router tip 48 carried on body 46. Body 46 is preferably made of a length of stainless steel tubing having a lumen communicating with the vacuum or suction source via transverse passage 34 and the suction channels of the handpiece. An open forward end of body 46 is joined to the router tip 48, and an open rearward end of the body defines the proximal end of the inner member adhesively secured to hub 22. If desired, the proximal end of body 46 can be externally knurled to enhance securement of the inner member to hub 22. A thin-walled bearing sleeve or tube 50 can be mounted, such as with a shrink fit, on body 46 adjacent the rearward end thereof to be disposed within outer member 12 when the inner and outer members are assembled, thereby stabilizing the inner and outer members and permitting the surgical router to withstand increased radial or side loads without misalignment or damage.

As shown in FIGS. 2-4, router tip 48 is preferably made in its entirety of 440 Series stainless steel having a hardness in the range of 52 to 57 Rc. Tip 48 includes a rearward or proximal section 52 and a forward or distal section 54 joined to proximal section 52 at a partially circumferential or semi-circumferential junction 56. Proximal section 52 includes a tubular neck 58 extending proximally from an annular shoulder 60 preferably beveled or angled to taper in the proximal direction. Neck 58 has an outer diameter adapted to be received in the forward end of body 46 with that forward end in abutment or substantially in abutment with shoulder 60. Body 46 and router tip 48 are joined, such as by laser welding or silver soldering, along shoulder 60, and a longitudinal passage 62 is formed partly through router tip 48 to communicate with the lumen of body 46. Passage 62 extends proximally through neck 58 and terminates distally at an internal wall 64 that converges in the distal direction to an end point 65 aligned with the longitudinal axis of the inner member and with a transverse plane containing junction 56. If desired, a thin-walled bearing sleeve or tube 66 (FIG. 1) can be disposed on the inner member to span shoulder 60 and the forward end of body 46 as described above for bearing sleeve 50. Proximal section 52 has an external size and configuration distally adjacent shoulder 60 to form a smooth, unitary, distal continuation or extension of body 46 such that body 46 and proximal section 52 can be considered as together forming a unitary proximal section of inner member 12 joined to distal section 54. As shown, proximal section 52 has a generally cylindrical external configuration distally adjacent shoulder 60 with an outer diameter the same or substantially the same as the outer diameter of body 46. Distal section 54 is preferably solid or substantially solid and is preferably formed integrally, unitarily with proximal section 52. Distal section 54 terminates proximally at junction 56 and distally at a closed forward end corresponding to inner member distal end 20.

A pair of router or cutting fingers or blades 70 is disposed on router tip 48 equally spaced about the longitudinal axis of inner member 14, and a pair of flutes 72 is disposed between the cutting blades 70. Each of the flutes 72 is defined by a bottom 74 extending longitudinally along router tip 48, a side 76 extending outwardly from bottom 74 in a generally radial direction transverse to bottom 74 and a curved or radiused connecting segment 78 joining bottom 74 to side 76. Side 76 and connecting segment 78 are curved in a counterclockwise direction about the inner member longitudinal axis. Each of the router blades 70 has a curved leading or inner wall 80 defined by the side 76 of an adjacent flute. A trailing or outer wall 82 is joined to the bottom 74 of an opposing flute. A side cutting surface 84 joins the leading wall 80 to the trailing wall 82. Clearance surface or wall 86 extends angularly, inwardly in the direction of the inner member longitudinal axis from the trailing wall 82 toward distal end 20. An end cutting surface 88 joins clearance wall 86 to leading wall 80. Side cutting surfaces 84 are angularly joined to leading walls 80 to define sharp side cutting edges 90, and end cutting surfaces 88 are angularly joined to leading walls 80 to define sharp end cutting edges 92. Router blades 80 are helically arranged on router tip 48 such that side cutting edges 90 define a helix angle H with the inner member longitudinal axis, and the connecting segments 78 extend along the inner member in the same helical direction as the side cutting edges. Blades 70 can be arranged on the router tip with a right hand helix, as shown, for cutting by the side and end cutting edges when the inner member 14 is rotated counterclockwise. Alternatively, the blades can be arranged on the router tip with a left hand helix for cutting in a clockwise direction, with the flute sides or router blade leading walls curved in the direction of rotation for the inner member in the outer member.

End cutting surfaces 88 and end cutting edges 92 meet at a central distal point or juncture 93 at distal end 20, the juncture 93 being aligned with the inner member longitudinal axis. End cutting edges 92 extend from juncture 93 in a direction outwardly of the inner member longitudinal axis to meet or merge with the side cutting edges 90 proximally of distal end 20. When viewed from the side as shown in FIG. 2, the end cutting edges 92 each define a straight or linear (or substantially straight or linear) segment 94 extending outwardly from juncture 93, and from a proximally curved segment 96 extending from straight segment 94, to meet or merge with side cutting edge 90 at a maximum or major outer diametric dimension D for router blades 70. When viewed in FIG. 3, the major diametric dimension extends diametrically from one side cutting edge 90 to the other along a diagonal line crossing the longitudinal axis of the inner member. The major diametric dimension corresponds to the major or maximum diameter of the outer circumferential surface of rotation or revolution defined by the side cutting edges 90 when the inner member is rotated counterclockwise. When viewed from the front or distally as shown in FIG. 3, end cutting edges 92 are curved in a counterclockwise direction about the inner member longitudinal axis in accordance with the curvature of leading walls 80.

Side cutting surfaces 84 have a width between leading walls 80 and trailing walls 82 in a direction transverse or perpendicular to the side cutting edges 90. The width of the side cutting surfaces 84 is uniform or constant (or substantially uniform or constant) along the length of the side cutting edges 90 as shown in FIG. 4, the side cutting edges 90 having a length from end cutting edges 92 to junction 56 (FIG. 2). For each router blade 70, a primary relief angle A defined between the side cutting surface 84 and a plane P1 containing the side cutting edge 90 and disposed tangential to the circumferential surface of rotation. A tip relief angle B is defined between the end cutting surface 88 and a plane P2 containing the inner member longitudinal axis. A rake angle C is defined between the plane P2 and a plane P3 containing the side cutting edge 90 and the inner member longitudinal axis at the major diametric dimension. If desired, the rake angle can be positive as shown or neutral.

The trailing walls 82 are curved about the inner member longitudinal axis from the flute bottoms 74 to the side cutting surfaces 84 in the direction of rotation of the inner member, i.e., counterclockwise looking at FIG. 3. Trailing walls 82 terminate distally at a pair of opposed ridges 97 and proximally at junction 56 with clearance surfaces 86 being joined to the trailing walls at the ridges. Ridges 97 are curved about the inner member longitudinal axis in accordance with the curvature of the trailing walls, and the radius of curvature for the trailing walls 82 at the ridges is non-uniform or non-constant with the curvature gradually decreasing from the flute bottoms 74 to the side cutting surfaces 84 from a maximum curvature $R^1$ to a minimum curvature $R^2$. The curvature of the trailing walls 82 gradually becomes uniform in the lengthwise direction from ridges 97 to junction 56 such that the trailing walls have a constant or uniform curvature at junction 56 corresponding to the curvature of the outer diameter of proximal section 52. The width of distal section 54, between trailing walls 82 in a direction transverse to the inner member longitudinal axis, tapers or decreases lengthwise or longitudinally in the distal direction from junction 56 to ridges 97, and from ridges 97 toward distal end 20. The distal section 54 is more gradually tapered from junction 56 to ridges 97, and more steeply tapered from ridges 97 toward distal end 20 in accordance with the relatively greater length of the distal section between junction 56 and ridges 97 than between ridges 97 and distal end 20. Clearance walls 86 extend angularly inwardly from the trailing walls 82 to end cutting surfaces 88 in accordance with the taper of distal section 54 from ridges 97 toward distal end 20. A minor diametric dimension $D^1$ for router blades 70, concentric with the major diametric dimension, is defined between ridges 97 along a diagonal line crossing the inner member longitudinal axis as shown in FIG. 3.

An end gash is provided on router tip 48 for center cutting and includes a pair of notches or indentations 98 disposed between clearance walls 86 and leading walls 80. Notches 98 define generally triangular or V-shaped center cutting surfaces 100 extending angularly inwardly in the distal direction from flute bottoms 74 to juncture 93. Center cutting surfaces 100 angularly join clearance walls 86 and leading walls 80 and have a width, between the clearance walls and the leading walls, that is tapered lengthwise from flute bottoms 74 to juncture 93. Center cutting edges 102 are formed by the juncture of center cutting surfaces 100 with clearance walls 86. These center cutting edges extend angularly, proximally from juncture 93, to terminate at flute bottoms 74 distally of the terminations of ridges 97 along the flute bottoms and laterally outwardly spaced from leading walls 80. In this manner the center cutting edges are angled from the leading walls and the end cutting edges in the direction of rotation of the inner member in the outer member.

Flutes 72 have a depth corresponding to the distance between bottoms 74 and side cutting edges 90 in a direction transverse or perpendicular to the side cutting edges. The flute depth, corresponding to the height of the router blades, tapers or decreases in a proximal direction from a maximum flute depth or router blade height at the major diametric dimension D. The width dimension of flutes 72, corresponding to the width of bottoms 74 in a direction transverse to the flute depth, increases in a proximal direction as shown in FIG. 4 from distal ends toward proximal ends of the flutes. Flute sides 76, corresponding to leading walls 80, are curved along the flute depth in a direction of rotation of the inner member in the outer member. The curvature of sides decreases in the proximal direction along the length of the flutes from a maximum curvature at a distal or forward end of the flutes. Flutes 72 extend lengthwise in a proximal direction beyond the side cutting edges 90 and along a portion of proximal section 52 containing passage 62. Flute bottoms 74 terminate distally at center cutting surfaces 100 with the flutes communicating with notches 98. The flute bottoms can have a slightly concave curvature that becomes flat at the flute proximal ends as shown in FIG. 3. The flute bottoms extend lengthwise in the proximal direction from center cutting surfaces 100 with an outward angle or curvature to merge with the outer diameter of proximal section 52 at the proximal flute ends disposed proximally of internal wall 64. Accordingly, flute bottoms 74 are disposed closer to the inner member longitudinal axis at the flute distal ends than at the flute proximal ends. The flute bottoms thus angularly intersect or cut through passage 62 such that aspiration ports, holes, apertures or openings 104 communicating with passage 62 are formed within the flutes along bottoms 74 at the flute proximal ends. Depending on the angle and depth at which the flute bottoms intersect passage 62, the aspiration ports 104 can be elongate, oval or elliptical and can be of a size to accommodate relatively large quantities and size of tissue and debris. The aspiration ports are integral and unitary with the flutes 72 and are substantially or partially aligned with one another in a direction transverse to the inner member longitudinal axis. Proximal section 52 has connecting walls 108 formed as proximal extensions or continuations of flute sides 76 and router leading walls 80. Edges 110 of connecting walls 108 are formed as proximal extensions or continuations of side cutting edges 90. The connecting walls 108 and edges 110 merge distally with the leading walls and side cutting edges, respectively, at junction 56 and proximally with the outer diameter of proximal section 52. Junction 56 can have a stepped configuration with trailing walls 82 disposed slightly inwardly of the outer diameter of proximal section 52. Junction 56 corresponds to solid segments of the circumference of the router tip 48 thereat with flutes 72 being disposed between the circumferential segments.

Preferably, the helix angle H is in the range of 7° to 15°, the primary relief angle A is in the range of 15° to 25°, the tip relief angle B is in the range of 15° to 20° and the width of the side cutting surfaces 84 is 0.020 inch. The major diametric dimension for cutting blades 70 is preferably 0.175 to 0.177 inch, and the minor diametric dimension is preferably approximately 0.085 inch. Flutes 72 preferably have a maximum depth of 0.075 inch and a length of 1.05 inches. The curved segments 96 of end cutting edges 92 preferably have a radius of curvature of 0.06 inch. Prior to assembly of inner member 14 in outer member 12, it is preferred that a coating of lubricant be applied to the outer diameter of the inner member and that a small amount of the lubricant be applied to the bearing surface of the thrust washer 40, where provided.

FIG. 5 illustrates a preferred process for forming flutes 72 and aspiration ports 104. Flutes 72 are preferably formed in router tip 48 via a grinding process; and, as shown in FIG. 5, a grinding wheel 112 is moved in a proximal direction from distal end 20 toward the outer diameter of proximal section 52 in accordance with the outward angle or curvature desired for flute bottoms 74. The grinding wheel is positioned at distal end 20 in accordance with the maximum flute depth and router blade height desired and is moved far enough proximally to cut into the passage 62, thereby forming aspiration ports 104 simultaneously with flutes 72. The grinding process is carried out at 180° spaced locations about the inner member longitudinal axis to obtain two equally spaced flutes 72 and router blades 70.

According to a preferred embodiment for the surgical router, outer member 12 has a length of 5.20 inches, an outer diameter of 0.221 inch and an inner diameter of 0.187 inch. Bore 24 of hub 18 has a length to receive outer member 12 with the distance from bearing surfaces 30 to peripheral edge 44 being 5.345 inches. Inner member 14 has a length of 6.475 inches and is secured to hub 22 such that the distance from thrust washer 40, where provided, to distal end 20 is 5,931 inches and the distance from lip 28 to distal end 20 is 5,941 inches. With thrust washer 40, or lip 28, engaged with bearing surface 30, the distance that the inner member 14 extends beyond peripheral edge 44 is preferably in the range of 0.581 to 0.591 inch. Body 46 has a length of 5.02 inches, an outer diameter of 0.184 inch and an inner diameter of 0.156 inch. Router tip 48 has a length of 1.58 inch. Proximal section 52 has a length of 0.994 inch including a length of 0.125 inch for neck 58 received in the lumen of body 46, and distal section 54 has a length from junction 56 to distal end 20 of 0.586 inch. Neck 58 has an outer diameter of 0.155 inch and an inner diameter of 0.125 inch. Shoulder 60 is beveled or angled 45° from the outer diameter of proximal section 52, and the outer diameter of proximal section 52 is 0.184 inch.

Figure 6:
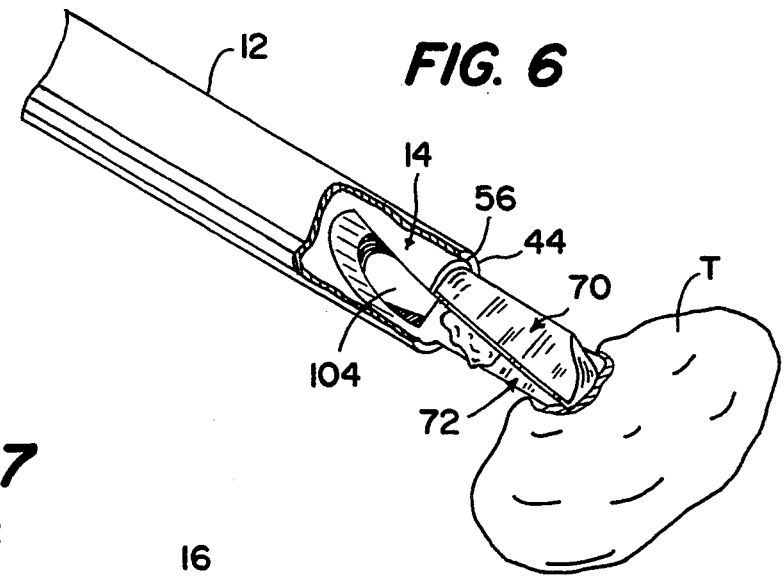
FIG. 6 is a broken perspective view of the surgical router of FIG. 1 in use cutting and aspirating anatomical tissue.

In use, inner member 14 is concentrically disposed in outer member 12, hub 22 being positioned in hub 18 with lip 28, or thrust washer 40, engaging bearing surface 30. With the inner member disposed within the outer member, distal section 54 of router tip 48 extends distally beyond the open distal end 18 of outer member 12 with aspiration ports 104 disposed within the outer member; and, preferably, junction 56 is aligned or substantially aligned with peripheral edge 44 as shown in FIG. 6. Driven tang 38 is coupled with the drive motor of the handpiece, and the inner member is rotated, counterclockwise looking distally, within the outer member in the direction of curvature of the leading walls 80. Suction is produced in the passage 62 via a source of suction or vacuum communicating with the suction channels in the handpiece and transverse passage 34. As shown in FIG. 6, the surgical router 10 can then be utilized to cut anatomical tissue T, including bone and cartilage, for example. The router can cut the tissue via the side, end and center cutting edges 90, 92 and 102 in various ways to perform various diverse cutting functions including shaving, resection, abrading, trimming and debriding, for example. The surgical router can be positioned and moved relative to the tissue T in various ways in accordance with the cut desired and/or the quantity of tissue desired to be removed. Fragments of tissue cut by the router blades and debris are captured by the flutes 72 and carried proximally therealong to the aspiration ports 104 for removal from the patient's body via passage 62 communicating with the aspiration ports and the suction channels of the handpiece. Surgical router 10 is particularly useful in closed or endoscopic procedures wherein access to a surgical site in the patient's body is gained via a portal sleeve positioned in a minimally sized opening or endoscopic portal formed in tissue of the body to provide communication with the surgical site from externally of the body. The configuration and profile of surgical router facilitates introduction of the surgical router at a surgical site within the body via the endoscopic portal and promotes movement ant manipulation of the router tip at the surgical site, which can be closedly confined, to cut tissue.

With the surgical router of the present invention, tissue cut by the router blades is carried proximally by the flutes and is immediately aspirated due to the aspiration ports being integral with the flutes. The radiused connecting segments joining the flute bottoms to the leading walls prevent build-up, load-up and clogging of the router tip by tissue fragments and debris and facilitate movement of cut tissue toward the aspiration ports. The tapered width of the distal section facilitates movement and manipulation of the surgical router relative to anatomical tissue to enhance various diverse cutting functions. The end and center cutting edges permit end and center cutting functions to be easily initiated and accomplished, thusly expanding the areas of use for the surgical router. The primary relief angle, tip relief angle and curvature of the router blades provide an aggressive cutting action while the flutes allow relatively large quantities of cut tissue and debris to be captured and directed toward the aspiration ports. The configuration of the aspiration ports facilitates aspiration of relatively large quantities and sizes of tissue to further reduce the possibility of clogging. The helical arrangement of the router blades and flutes further enhance cutting by the cutting edges and movement of cut tissue and debris proximally toward the aspiration ports.

In accordance with the present invention, it is believed that other modifications, variations and changes will be suggested to those skilled in the art in view of the teachings set forth herein. It is therefore understood that all such variations, modifications and changes are believed to fall within the scope of the present invention as defined by the appended claims.

What is claimed is:

1. A surgical router comprising:
   an elongate outer tubular member having a distal end and a proximal end;
   an elongate inner member rotatably disposed in said outer member and having a distal section protruding distally beyond said outer member distal end, a proximal end and a longitudinal axis;
   a pair of cutting blades on said distal section equally spaced about said axis and having cutting edges for cutting anatomical tissue;
   a pair of flutes on said inner member disposed between said cutting blades for carrying anatomical tissue cut by said cutting blades;
   a pair of aspiration ports defined in said inner member, each aspiration port disposed within a respective one of said flutes; and
   a passage in said inner member communicating with said aspiration ports and a source of suction for aspirating cut tissue through the surgical router.

2. A surgical router as recited in claim 1 wherein said cutting blades protrude distally beyond said outer member distal end, said flutes extend proximally of said cutting edges and said aspiration ports are disposed within said flutes proximally of said cutting edges.

3. A surgical router as recited in claim 2 wherein each of said flutes has a bottom, a side extending transverse to said bottom and a curved connecting segment joining said bottom and said side, said connecting segments being curved about said longitudinal axis in the direction of rotation of said inner member in said outer member, said aspiration ports being disposed in said flute bottoms.

4. A surgical router as recited in claim 3 wherein said cutting edges extend longitudinally, helically along said distal section in a proximal direction.

5. A surgical router as recited in claim 4 wherein said connecting segments extend longitudinally along said inner member in the same helical direction as said cutting edges, said flutes have distal ends and proximal ends and said bottoms are disposed closer to said axis at said flute distal ends than at said flute proximal ends.

6. A surgical router as recited in claim 5 wherein said inner member includes a proximal section joined to said distal section, said proximal section has an outer diameter to be received within said outer tubular member and said flute bottoms merge with said outer diameter at said flute proximal ends.

7. A surgical router as recited in claim 6 wherein said passage is disposed in said proximal section and said flute bottoms angularly intersect said passage to form said aspiration ports in said proximal section.

8. A surgical router as recited in claim 7 wherein said flutes have a depth between said flute bottoms and said cutting edges and a length and said flute depth decreases in a proximal direction along said flute length.

9. A surgical router as recited in claim 8 wherein said cutting edges are disposed along said flute sides, and said flute sides are curved in the direction of rotation of said inner member in said outer member.

10. A surgical router as recited in claim 9 wherein said flutes have a width in a direction transverse to said flute depth, and said flute width increases in a proximal direction along said flute length.

11. A surgical router as recited in claim 1 wherein said distal section of said inner member has a distal end, and wherein said cutting edges are end cutting edges extending from said distal section distal end outwardly of said longitudinal axis to a major diametric dimension of said cutting blades.

12. A surgical router as recited in claim 11 further comprising side cutting edges joined to said end cutting edges at said major diametric dimension and longitudinally, helically along said inner member in a proximal direction.

13. A surgical router as recited in claim 12 further comprising center cutting edges extending angularly, proximally from said distal end, said center cutting edges being angled from said end cutting edges in the direction of rotation of said inner member.

14. A surgical router comprising:
   an elongate outer tubular member having a distal end and a proximal end;
   an elongate inner tubular member rotatably disposed in said outer member and having a distal end disposed distally of said outer member distal end, a proximal end and a longitudinal axis;
   a pair of cutting blades on said inner member equally spaced about said axis and extending from said inner member distal end in a proximal direction and a pair of flutes disposed between said cutting blades, each of said flutes having a bottom and a side transverse to said flute bottom, said cutting blades having leading walls defined by said flute sides, side cutting edges along said leading walls extending longitudinally, helically along said inner member and defining a major diametric dimension for said cutting blades, end cutting edges along said leading walls extending distally from said side cutting edges to a point at said distal end aligned with said axis and trailing walls extending between said leading walls and said flute bottoms, said leading walls being curved about said axis in the direction of rotation of said inner member in said outer member for cutting of anatomical tissue by said side and end cutting edges; and
   means in said inner member for aspirating tissue cut by said cutting blades through said inner member.

15. A surgical router as recited in claim 14 wherein said trailing walls terminate distally at opposed ridges disposed proximally of said distal end and further including clearance walls joined to said trailing walls at said ridges and extending angularly, inwardly from said trailing walls in the direction of said longitudinal axis.

16. A surgical router as recited in claim 15 wherein said inner member includes a proximal section, a distal section joined to said proximal section at a junction, a width between said trailing walls in a direction transverse to said axis, said width being tapered from said junction to said ridges and from said ridges to said distal end with said taper of said width from said ridges to said distal end being greater than said taper of said width from said junction to said ridges.

17. A surgical router as recited in claim 16 wherein said end cutting edges merge with said side cutting edges at said major diametric dimension and said major diametric dimension corresponds to a circumferential surface of rotation defined by said cutting blades when said inner member is rotated in said outer member.

18. A surgical router as recited in claim 17 wherein said ridges define a minor diametric dimension for said cutting blades concentric with said major diametric dimension.

19. A surgical router as recited in claim 18 wherein said cutting blades have a height between said flute bottoms and said side cutting edges and said blade height decreases in a proximal direction from a maximum blade height at said major diametric dimension.

20. A surgical router as recited in claim 19 wherein said leading walls extend between said distal end and said junction and the curvature of said leading walls in the direction of rotation of said inner member decreases in a proximal direction between said distal end said junction.

21. A surgical router as recited in claim 20 wherein said trailing walls have a length between said junction and said ridges and further including side cutting surfaces joined to said leading walls and said trailing walls, said side cutting edges being defined by the juncture of said side cutting surfaces with said leading walls, said side cutting surfaces having a width between said leading walls and said trailing walls that is substantially uniform along said length of said trailing walls.

22. A surgical router as recited in claim 21 wherein said trailing walls are curved about said axis between said flute bottoms and said side cutting surfaces in the direction of rotation of said inner member in said outer member and said curvature of said trailing walls at said ridges decreases between said flute bottoms and said side cutting surfaces.

23. A surgical router as recited in claim 22 wherein said curvature of said trailing walls is uniform at said junction.

24. A surgical router as recited in claim 23 wherein said proximal section has an outer diameter and said trailing walls merge with said outer diameter at said junction.

25. A surgical router as recited in claim 24 wherein said side cutting surfaces define a primary relief angle with a plane containing said side cutting edges and disposed tangential to said circumferential surface of rotation and said primary relief angle is in the angle of fifteen to twenty-five degrees.

26. A surgical router as recited in claim 25 and further including end cutting surfaces joined to said leading walls and said clearance walls, said end cutting edges being defined by the juncture of said end cutting surfaces with said leading walls, and a tip relief angle defined between said end cutting surfaces and a plane containing said longitudinal axis, said tip relief angle being in the range of fifteen to twenty degrees.

27. A surgical router as recited in claim 26 wherein said side cutting edges define a helix angle with said longitudinal axis that is in the range of seven to fifteen degrees.

28. A surgical router as recited in claim 27 wherein a rake angle is defined between said plane containing said longitudinal axis and a plane containing said side cutting edges and intersecting said plane containing said longitudinal axis that is the range of five to ten degrees.

29. A surgical router as recited in claim 14 wherein said means for aspirating tissue comprises:
   a pair of aspiration ports defined in said inner member, each aspiration port disposed with a respective one of said flutes; and
   a passage in said inner member for aspirating cut tissue through aspiration ports to externally of said router.

30. A surgical router comprising:
   an elongate outer tubular member having a distal end and a proximal end;
   an elongate inner tubular member rotatably disposed in said outer member and having a distal end, a longitudinal axis, a pair of router blades equally spaced about said axis disposed distally beyond said outer member distal end and a pair of flutes disposed between said router blades, said flutes having bottoms and sides transverse to said flute bottoms, said router blades having end cutting edges extending from said inner member distal end in a direction outwardly of said longitudinal axis to a major diametric dimension for said router blades, side cutting edges joined to said end cutting edges at said major diametric dimension and extending longitudinally, helically along said inner member in a proximal direction and center cutting edges extending angularly, proximally from said distal end, said center cutting edges being angled from said end cutting edges in the direction of rotation of said inner member in said outer member and terminating proximally at said flute bottoms; and
   means in said flutes for aspirating anatomical tissue cut by said router blades when said inner member is rotated in said outer member.

31. A surgical router as recited in claim 30 wherein said router blades further include a pair of leading walls having said end and side cutting edges thereon, said leading walls having a height extending in a direction radially outwardly of said longitudinal axis and a length extending from said inner member distal end toward said inner member proximal end, a pair of trailing walls extending between said flute bottoms and said leading walls and having a length terminating distally at ridges disposed proximally of said inner member distal end, clearance walls extending between said trailing walls and said distal end and a pair of notches on said inner member distal end disposed between said clearance walls and said leading walls in communication with said flutes.

32. A surgical router as recited in claim 31 wherein said notches define center cutting surfaces extending angularly outwardly from a distal point aligned with said axis to said flute bottoms and said center cutting edges are defined by the juncture of said center cutting surfaces with said clearance walls.

33. A surgical router as recited in claim 32 wherein said center cutting surfaces have a width between said clearance walls and said leading walls that is tapered from said flute bottoms to said distal point.

* * * * *